United States Patent [19]

Henrio et al.

[11] Patent Number: 5,714,095
[45] Date of Patent: Feb. 3, 1998

[54] COMPOSITION FOR CHLORINE-CONTAINING POLYMER BASED ON BETA-DIKETONE AND ACETYLACETONATE

[75] Inventors: Françoise Henrio, Morainvilliers; Michel Gay, Villeurbanne; Gilles Mur, Saint Maur des Fosses, all of France

[73] Assignee: Rhone-Poulenc Chimie, Courbevoie Cedex, France

[21] Appl. No.: 662,938

[22] Filed: Jun. 12, 1996

[30] Foreign Application Priority Data

Jun. 14, 1995 [FR] France ................. 95 07089

[51] Int. Cl.$^6$ .................. C09K 15/06; C09K 15/32; C08L 27/00
[52] U.S. Cl. .............. 252/407; 252/400.52; 252/400.61; 524/357; 524/399; 524/400; 524/567
[58] Field of Search ................. 524/567, 399, 524/400, 431; 252/399, 400.52, 400.61, 407

[56] References Cited

U.S. PATENT DOCUMENTS

| | | | |
|---|---|---|---|
| 4,102,839 | 7/1978 | Crochemore et al. | 524/399 |
| 4,221,687 | 9/1980 | Minagawa et al. | 524/567 |
| 4,427,816 | 1/1984 | Aoki et al. | 524/567 |
| 4,748,166 | 5/1988 | Gautier et al. | 524/431 |
| 5,034,443 | 7/1991 | Bae et al. | 524/399 |
| 5,141,983 | 8/1992 | Hasegawa | 524/457 |

FOREIGN PATENT DOCUMENTS

| | | |
|---|---|---|
| 0046161 | 2/1982 | European Pat. Off. . |
| 0596809 | 5/1994 | European Pat. Off. . |
| 0658592 | 6/1995 | European Pat. Off. . |
| 41 34 325 | 4/1993 | Germany . |

*Primary Examiner*—Tae Yoon
*Attorney, Agent, or Firm*—Burns, Doane, Swecker & Mathis, L.L.P.

[57] ABSTRACT

The invention relates to compositions for chlorine-containing polymer such as PVC, including a stabilizing composition.

According to the invention the stabilizing composition includes:

a) the unpurified crude product resulting from the reaction of condensation of an ester with a ketone in the presence of an alkaline agent, this crude product including between 10 and 95%, preferably between 20 and 80% by weight of beta-diketone, and b) a metal acetylacetonate complex, the ratio of the constituents a/b being between 50/50 and 1/99.

The invention also relates to the standard objects obtained from these compositions.

20 Claims, No Drawings

COMPOSITION FOR CHLORINE-CONTAINING POLYMER BASED ON BETA-DIKETONE AND ACETYLACETONATE

The present invention relates to compositions for chlorine-containing polymer including a stabilizing composition and to the standard objects obtained from the said compositions.

Beta-diketones today form part of the best organic stabilizers for chlorine-containing polymers such as PVC. This is why these compounds have become increasingly important from the commercial viewpoint.

The cost of manufacture of these beta-diketones is therefore an important factor which can, in particular, restrict their development. In fact, it is economically quite unthinkable to employ stabilizers which are too costly in the industry of chlorine-containing polymers and especially that of PVC.

Furthermore, to stabilize this type of polymer, it is also known to use metal complexes of dicarbonyl compounds. They are in particular calcium or zinc chelates of compounds capable of keto-enol tautomerism, such as beta-keto esters or beta-diketones.

Ethyl acetylacetate or acetylacetone may be mentioned among these compounds.

These chelates generally form part of more complex compositions which also include other constituents such as calcium or zinc salts, optionally associated with another HCl-acceptor, and superbasic compounds (phenolate, sulphonate), hydrotalcites, phosphites, ortho esters, polyols and the like.

More recently, patent application DE-A-4 134 325 (Henkel) has described stabilizing compositions including especially a calcium complex of a beta-diketone, such as calcium acetylacetonate, a zinc salt, a beta-diketone, an inorganic costabilizer and a polyol.

The objective of the present invention is to provide a composition exhibiting improved properties in respect of its stabilizing action from the view point of temperature and ultraviolet rays, and which is easily available and inexpensive.

To this end, the subject of the invention is a composition for chlorine-containing polymer such as especially PVC, characterized in that it includes, as stabilizing composition:

a) the unpurified crude product resulting from the reaction of condensation of an ester with a ketone in the presence of an alkaline agent, this crude product containing between 10 and 95%, preferably between 20 and 80% by weight of beta-diketone, and b) a metal acetylacetonate complex, the ratio of the constituents a/b being between 50/50 and 1/99.

The invention also relates to the standard objects obtained from this composition.

After having carried out long and costly research, the Applicant Company has found, quite unexpectedly, that a stabilizing composition for chlorine-containing polymer (PVC) including the unpurified crude product (a) resulting from the reaction of condensation of an ester with a ketone in the presence of an alkaline agent, in association with the acetylacetonate, has, at identical weight, a stabilizing action which is at least equal to that which a similar stabilizing composition containing recrystalized purified beta-diketone would have had, everything else being otherwise equal.

The abovementioned crude product includes between 10 and 95%, preferably between 20 and 80% by weight of beta-diketone and can be employed in solid form.

The reaction of condensation of an ester with a ketone can be written:

$$R_1COCHR_2H + R_3CO\text{—}OR_4 + ACat \rightarrow R_1COCHR_2COR_3 + R_4OH$$

with:

ACat is chosen from an emide of a cation or a hydride of a cation;

each of $R_1$ and $R_3$, which may be identical or different, denotes a hydrocarbon radical advantageously containing from 1 to 30 carbon atoms, preferably from 1 to 18 carbon atoms;

$R_2$ is a hydrogen or a hydrocarbon, generally alkyl, radical advantageously containing not more than 4 carbon atoms;

$R_1$ and $R_2$ may be linked so that the beta-diketone forms a ring;

$R_4$ denotes a hydrocarbon radical.

A wide spectrum of radicals may be employed where $R_1$, $R_2$ and $R_3$ are concerned.

Thus, $R_1$ and $R_3$, which are identical or different, may denote:

a linear or branched aralkyl or alkenyl radical containing up to 24 carbon atoms;

an aralkyl radical containing from 7 to 10 carbon atoms;

an aryl or cycloaliphatic radical containing fewer than 14 carbon atoms, it being possible for the cycloaliphatic radicals optionally to contain carbon-carbon double bonds.

These radicals may be substituted or unsubstituted for example by halogen atoms or, in the case of aryl or cycloaliphatic radicals, by methyl or ethyl groups.

The radicals listed above may also be modified by the presence in the aliphatic chain of one or more groups of formula:

$$\text{—O—}, \text{—CO—O—}, \text{—CO—}$$

$R_1$ and $R_3$ may also together denote a single divalent radical containing from 2 to 5 carbon atoms and which may contain an oxygen or nitrogen heteroatom;

$R_2$ may be:

a hydrogen atom (preferred case)

an alkyl radical, substituted or unsubstituted containing from 1 to 4 carbon atoms and which may be interrupted by —O—, —CO—O and —CO— groups.

$R_4$ denotes an alkyl radical containing from 1 to 4 carbon atoms, preferably methyl.

The cation Cat is generally an alkali metal, preferably sodium.

The condensation reaction described above is well known to a person skilled in the art and is described more particularly, especially in the following publications:

R. Hauser et al., "The acylation of ketones to form diketones", Organic Reactions - Vol. VII, Chapter 3, p.59–196, John Wiley, Publ. New York (1954)

Wiedman et al., C.r. 238 (1954), p. 699,

Morgan et al., Ber. 58 (1925), p. 333,

Livingstone et al., Am. Soc. 46 (1924), p. 881–888

Robert Levine et al., Am. Soc. 67 (1945), p. 1510–1517, which are incorporated as references into the present description.

According to a preferred embodiment the choice of the starting reactants is based on the availability of these products and on the activity of the reaction products obtained; thus, an ester is employed as preferred starting material:

in the case of the ester, methyl stearate, especially of technical grade, which may then contain other fatty acid esters including, in particular, methyl palmirate, in the case of ketone, acetophenone, and in the case of the alkaline agent, sodamide.

It is recommended to employ 2 moles of amide per mole of ester or of ketone introduced and to employ a slight molar excess (between 5 and 30%) of ketone in relation to the ester.

Because of the presence of sodamide it is preferable to perform the reaction under inert atmosphere, preferably under nitrogen purging.

The reaction is performed at a temperature which preferably lies between 30 and 60° C. At the ambient temperature (20°) the kinetics are too slow. In addition, if the temperature is too high, for example 60° C. and more, such a temperature promotes, on the one hand, the autocondensation of the ketones in general and of acetophenone in particular and, on the other hand, the formation of amides.

The solvents which can be employed are inert solvents of the ether type, especially isopropyl ether, aliphatic hydrocarbons (for example cyclohexane) or else aromatic hydrocarbons (toluene).

Although it is technically possible to conduct the reaction at a pressure which is higher than the atmospheric pressure, it is preferred, for economic reasons, to work at atmospheric pressure or else at a reduced pressure, so as to lower the temperatures shown above and to bring them into a range of between 35° and 55° C. Pressures lower than $10^4$ Pa are rarely employed.

At the end of reaction, the mixture is acidified. To do this, the reaction solution is poured into an aqueous solution of an acid, the preferred ones being acetic acid, hydrochloric acid and sulphuric acid. The pH of the aqueous layer is adjusted to a value which is preferably between 1 and 3.

The following 3 procedures may, in particular, be envisaged for introducing the reactants:

a) the enol anion of acetophenone is formed first by running the acetophenone into the amide/solvent mixture, and the ester is then added, b) the solvent, the amide and all of the ester are charged and then the acetophenone is run in slowly, c) the acetophenone and the ester are run simultaneously into the amide/solvent mixture.

It is recommended to employ route b) and then to acidify the reaction mixture in a molar excess (1.2- to 2-fold molar) of sulphuric acid diluted to 5–20% in water so that the pH is approximately 1.5.

After at least one washing with water, the solvent is removed by any suitable means, for example by evaporation, and a crude product which is solid at ambient temperature is obtained, generally containing between 40% and 90% by weight of beta-diketone.

According to an alternative form of the invention this crude product, once ground and reduced to powder form, can be employed directly as additive in a stabilizing composition for chlorine-containing polymer.

This powder has a particle size which is generally smaller than 500 µm, preferably smaller than 200µm.

Any techniques that are known to a person skilled in the art for obtaining powders can be employed so as to arrive at the desired particle size, and especially:

a) precipitation in a solvent, b) cryogenic grinding, c) spray-drying in a cold stream, countercurrentwise or con-currently.

According to technique a) the solid crude reaction product is dissolved in a suitable solvent like, for example, ethanol or methanol, at ambient temperature, the solvent is distilled off at a reduced pressure of the order of $10^3$ Pa and nitrogen is then injected.

According to technique b) liquid nitrogen and the crude reaction product in the form of pieces from a few millimeters to a few centimeters, obtained by coarse grinding or else by the technique of "flaking" the reaction solution, are introduced into a mill. The "flaking" allows the solvent to be removed from this reaction solution by passing the solution over a continuously cold rotating drum. The product solidified at the surface of the drum is recovered by a doctor blade precisely in "flake" form. Another inert liquid gas, such as liquid $CO_2$, may be used instead of liquid nitrogen.

According to technique c) the crude reaction product in the molten state is sprayed through a counter-current or a concurrent stream of a gas which is inert towards the product, such as oxygen-depleted air. Micro-beads of product are recovered, the particle size of which can be easily smaller than 100 µm and may range down to 10 µm.

According to a well-known technique the crude reaction product may be recrystalized from a suitable organic solvent, generally ethanol. The recrystalized product, separated from the mother liquors by simple filtration, is in the form of powder and is essentially made of beta-diketones. For some applications it is necessary to employ purified beta-diketones. The use of beta-diketones purified to more than 95% by weight in stabilizing compositions for graft polymer does not form part of the present invention.

On the other hand, according to another aspect of the invention, it has been found that, after removal of the solvent of crystalization by any suitable method (for example by evaporation or by the abovementioned flaking technique), the mother liquors produce a solid recrystalization residue which then generally contains at least 10% and in most cases between 20 and 40% of beta-diketones and that this crystalization residue, which can be converted into powder form, exhibits, in combination with the acetylacetonate, a stabilizing action on polymers which is similar to that which the same weight of a stabilizing composition based on recrystalized purified beta-diketone would have had.

These solid heavy residues from recrystalization are employed in the same way as the crude reaction product and can be reduced to powder by the same methods.

According to the invention the constituent (a), namely either the unpurified beta-diketone or the heavy residues from recrystalization, as mentioned above, are employed as a mixture with the acetylacetonate (b).

The acetylacetonate is advantageously in the form of calcium or zinc complex.

It may be, in particular, a complex made up of one mole of calcium hydroxide $Ca(OH)_2$ and of two moles of acetylacetone.

The stabilizing composition in accordance with the invention advantageously includes more acetylacetonate (b) than unpurified beta-diketone (a). The ratio of the constituents a/b is between 50/50 and 1/99 and preferably between 20/80 and 1/99.

In most cases a satisfactory stabilisation of chlorine-containing polymers and more particularly of PVC requires the combined use of several stabilizers which act in a complementary and sometimes synergistic manner.

The compositions according to the invention thus preferably contain a white pigment for its optical properties. According to a preferred alternative form of the invention the addition of $TiO_2$ makes it possible to improve, surprisingly and substantially, the whitness/light-resistance compromise and in particular the well-known phenomenon of turning pink. In accordance with the invention it is recommended to employ rutile $TiO_2$ whose particle size is generally between 0.1 and 0.5 μm. The addition of 0.5 to 10 parts and preferably 3 to 8 parts by weight of rutile $TiO_2$ per 100 parts of additive-free PVC is advantageously envisaged.

In addition to the crude reaction product and/or the heavy recrystalization residues and the acetylacetonate, the stabilizing compositions according to the invention may also contain an effective quantity of at least one additive chosen especially from:

a) an aluminium and/or magnesium sulphate and/or carbonate, especially of the hydrotalcite type. Such products are described, for example, in patents U.S. Pat. No. 4,299, 759, U.S. Pat. No. 4,427,816, EP-A-453 379 and EP-A-509 864;

b) a synthetic crystalline alkali metal alumino-silicate exhibiting a water content of between 13 and 25% by weight, of the composition $0.7–1.1M_2O.Al_2O_3.1.3–2.4SiO_2$, in which M symbolizes an alkali metal, especially sodium (DE-A-4 134 325 and U.S. Pat. No. 4,540,233), like, in particular, the zeolites of NaA type as described, for example in patent US-A-4 590 233;

c) an alcohol or an organic polyol in accordance with the teaching of FR-A-2 356 674 and FR-A-2 356 695 and/or an isocyanate (DE-A-4 134 325);

d) a salt of a metal chosen from calcium, barium, magnesium and strontium (EP-A-391 311);

e) an organic zinc compound (EP-A-391 811);

f) an organic phosphite, especially trialkyl or alkyl phenyl or triphenyl phosphites (EP-A-391 811) or an aluminium-calcium-hydroxy-phosphite complex as defined in DE-A-4 134 325 or else a calcium phosphite as described in U.S. Pat. No. 5,084,499;

g) epoxides, which are generally complex compounds, usually epoxidized polyglycerides, epoxidized linseed oil and epoxidized fish oils;

h) usual adjuvants such as phenolic antioxidants and anti-UV agents such as benzophenones, benzotriazoles or sterically hindered amines (usually known as Hals).

According to a particularly advantageous alternative form of the invention the crude product (a) is ground according to a particle size similar to that of the finest additional stabilizing additive present in the stabilizing composition. This additive may be, for example, an aluminium and/or magnesium carbonate and/or sulphate, for example of the hydrotalcite type and may then exhibit a particle size smaller than 100 μm, generally between 1 and 50 μm or else may be a calcium and/or barium stearate and may then also exhibit a particle size smaller than 100 μm, generally between 10 and 100 μm.

In general, any type of PVC is suitable, whatever its method of preparation: bulk, suspension, emulsion or any other type of polymerization, and whatever its intrinsic viscosity.

Vinyl chloride homopolymers may also be chemically modified, for example by chlorination. Many vinyl chloride copolymers may also be stabilized against the effects of heat, that is to say yellowing and degradation. These are, in particular, the copolymers obtained by copolymerization of vinyl chloride with other monomers containing a polymerizable ethylenic bond, like, for example, vinyl acetate or vinylidene chloride, maleic or fumaric acids or their esters, olefins such as ethylene, propylene and hexene, acrylic or methacrylic esters, styrene, and vinyl ethers, such as vinyl dodecyl ether.

These copolymers usually contain at least 50% by weight of vinyl chloride units and preferably at least 80% by weight of vinyl chloride units.

The compositions according to the invention may also contain mixtures based on chlorine-containing polymer containing minor quantities of other polymers, like halogenated polyolefins or acrylonitrile-butadiene-styrene copolymers.

PVC alone or mixed with other polymers is the chlorine-containing polymer most widely employed according to the invention.

The compositions of the invention are more particularly suitable for the preparation of rigid formulations, that is to say without plasticizer, or semirigid ones, that is to say with low plasticizer contents, such as for applications in building, the manufacture of various sections and bottle manufacture.

In most cases these formulations contain an impact-improver, such as lauryl acrylate/methyl methacrylate or butyl acrylate/methyl methacrylate copolymers.

They may also be plasticized formulations such as for the manufacture of films for agricultural use.

The plasticizers employed are known compounds such as, for example, alkyl phthalates. The most commonly employed one is di(2-ethylhexyl) phthalate, (usually called dioctyl phthalate).

When the compositions contain a plasticizer the content of the latter is generally from 5% to 120% by weight relative to the weight of chlorine-containing polymer.

Any of the usual methods for incorporating various stabilizers or adjuvants into the polymer may be employed. For example, the homogenization of the polymeric composition may be carried out on a roll mill or mixer, at a temperature such that the composition becomes fluid, normally between 150° C. and 200° C. in the case of PVC and for a sufficient period, of the order of a few minutes to a few tens of minutes.

The proportion of incorporation of the various stabilizers or adjuvants is usually low in relation to the chlorine-containing polymer.

It may thus be advantageous to prepare a premix of 2 or more of the constituent compounds of the compositions according to the invention before they are incorporated into the chlorine-containing polymer.

The chlorine-containing polymer, and more particularly PVC, compositions may be processed according to all the techniques usually employed, like, for example, extrusion, injection, extrusion blowing, calendering or rotational moulding.

The examples which follow illustrate the invention.

Unless indicated expressly otherwise, in what follows or what precedes, the parts and percentages are given by weight.

EXAMPLE 1: Preparation of the crude reaction product P1.

260 ml of toluene are introduced into a 2000-cm³ reactor fitted with a condenser, with good stirring and with the possibility of being connected either to vacuum or to a source of nitrogen, followed by 78 g of $NaNH_2$ under a nitrogen blanket.

The temperature of the mixture is then raised to 40° C. and then maintained at this temperature throughout the reaction and the finishing.

The whole apparatus is put at a pressure of $7×10^4$ Pa.

310 g of technical methyl stearate (containing 10% of methyl palmirate) are run in.

120 g of acetophenone are run in over 3 hours.

When the addition of the acetophenone is finished, the reaction mixture is left stirred for 45 min (temperature of 40° C. and under pressure of $7×10^4$ Pa).

The toluene solution is then run warm into a solution of 10% dilute sulphuric acid so that the pH of the aqueous layer after separation is 1.5.

After two washings the toluene solution is next evaporated by hydrodistillation at atmospheric pressure. The residue is then passed onto a continuously cooled rotating drum, to give a crude product P1 in the form of "flakes" that is 420 g of a product which is solid at 20° C., assaying at 78% of beta-diketones (82% yield, GC chromatographic analysis).

Example 2: Preparation of a P1 powder.

One part/hour of product P1 of example 1 and 0.3 parts/hour of liquid nitrogen are introduced by means of a screw conveyor into a hammer mill equipped with a 1-mm grid. The ground product is recovered by pneumatic conveying towards a separation system with a filter and a white powder of 50-μm particle size is obtained.

A similar powder is obtained when liquid nitrogen is replaced with liquid $CO_2$.

EXAMPLE 3: Thermal stability.

The starting point is the following PVC composition (rigid formulation):

| | |
|---|---|
| PVC powder prepared by suspension polymerization and marketed under the name S110P (Atochem): | 100 parts |
| Calcium stearate, stabilizer marketed by Atochem under reference Stavinor PSME: | 0.3 parts |
| Zinc stearate, stabilizer marketed by Atochem under reference ZN70.: | 1 parts |
| Didecyl phenyl phosphite, stabilizer marketed by Ciba-Geigy under reference Irgastab CH 300: | 0.5 parts |
| Polyvinyl alcohol, stabilizer marketed by RP Chimie under reference Rhodiastab PVAL: | 0.2 parts |
| Hydrotalcite (aluminium magnesium hydrogencarbonate), stabilizer marketed under reference Alcamizer 4 by Mitsui: | 0.6 parts |
| Ground calcium carbonate, filler marketed under reference Omyalite 95T by Omya: | 5 parts |
| Rutile titanium oxide pigment of particle size between 0.1 and 0.5 μm: | 6 parts |
| Impact improver (acrylic polymer), marketed by Rohm and Haas under the name Paraloid KM 355: | 6.5 parts |
| Lubricants marketed by Henkel under the names: | |
| Loxiol G60 (ester of an aromatic di acid and of an aliphatic fatty alcohol): | 0.4 parts |
| Loxiol G22 (paraffin wax): | 0.2 parts |
| A processing aid (marketed by Rohm and Haas Paraloid: | 1 parts |

Three samples are produced from this composition by adding:

$S_1$/0.30 parts of product P1 of Example 2

$S_2$/0.30 parts of product P2 (P2 =calcium acetylacetonate)

$S_3$/0.1 parts of product P1 and 0.2 parts of product P2 (formulation in accordance with the invention).

Each sample is homogenized in a Papenmeier-type fast mixer at a speed of 1800 rev/min up to a temperature of 115° C.

Starting with these powders an evaluation of the dynamic heat stability is performed with the Brabender® Plastograph. This apparatus consists:

of an electrical motor system coupled to a continuous or noncontinuous speed controller (0 to 200 rev/min);

of a thermostated bath with electronic proportional temperature control using silicone oil;

of a mixer, provided with a jacketed vessel, permitting heating by circulation of silicone oil, and of 2 rotors fastened by a bayonet locking system;

of a stop-clock.

Each test is introduced into this mixer at 150° C. in a proportion of 53 g, with the aid of a hopper and of a plunger propelled by a 5-kg weight. A sample is then taken every 5 minutes in order to obtain a pellet, until the PVC mix is blackened or scorched.

The yellowing index, parameter b of the (L, a, b) system is measured on each pellet by colouring with the aid of a Minolta CR 200® colorimeter.

The thermal degradation of each formula $S_1$, $S_2$ or $S_3$ as a function of time is thus obtained.

The results obtained are listed together in Table 1 below:

TABLE 1

| Time | $S_1$ | $S_2$ | $S_3$ |
|---|---|---|---|
| 5 min | 3.3 | 2.9 | 2.9 |
| 10 min | 4.6 | 4.1 | 3.9 |
| 15 min | 5.1 | 5.2 | 5.1 |
| 20 min | 5.8 | 15.8 | 12.9 |

Inspection of table 1 shows that sample $S_1$ has a better thermal stability than sample $S_2$.

Composition $S_3$ has both the initial good colour (at 5 minutes) of formula $S_2$ and the good colour stability of formula $S_1$.

EXAMPLE 4: Colour and gloss.

Three samples $S_1$, $S_2$ and $S_3$ are prepared as in Example 3.

Starting with these powders, a conversion by extrusion is carried out in order to obtain sheets.

The characteristics of the single-screw extruder are:

Manufacturer: Andouart.

Conical screw:
 compression ratio=2.8
 length/diameter ratio=20
 diameter D=40 mm The extrusion conditions are:

Speed of rotation of the screw=23 rev/min

Temperature profile:

| Zone 1 | 2 | 3 | Dies |
|---|---|---|---|
| 175° C. | 180° C. | 185° C. | 190° C. |

The colorimetric properties are measured according to the CIE (L, a, b) colorimetric system described above in Example 3, and the gloss at an angle of incidence with a value of 60°.

The results obtained are listed together in Table 2, which follows:

TABLE 2

|  | $S_1$ | $S_2$ | $S_3$ |
| --- | --- | --- | --- |
| L | 94.1 | 94.9 | 94.8 |
| a | 1.53 | 0.76 | 0.70 |
| b | 8.78 | 4.50 | 4.60 |
| Gloss | 45 | 45 | 57 |

From this Table 2 it is deduced that, where the colour is concerned, $S_2$ and $S_3$ are similar and better than $S_1$. On the other hand, with regard to the gloss, $S_3$ is much better than $S_1$ and $S_2$.

Example 5: Pink colouring.

The procedure is as in Example 4.

The extruded sheets are subjected to a test for pink colouring in the following conditions:

The samples are subjected to a 200-hour cycle of UV radiation in the UVCON conditions:

Atlas UVCON apparatus

Illumination spectrum:

UVA with a maximum at $\lambda=340$ nm and filter<290 nm

Black body temperature=55° C.

They are then left for 24 hours without UV radiation in a ventilated oven at 70° C.

The sensitivity of each formulation to pink colouring as a function of time is thus obtained. This sensitivity is measured by the change $\Delta a$, a being the abovementioned parameter of the CIE (L, a, b) system.

The results obtained are listed together in Table 3 below:

|  | $S_1$ | $S_2$ | $S_3$ |
| --- | --- | --- | --- |
| $\Delta a$ | 3.00 | 0.70 | 0.90 |

From this Table 3 it emerges that the formulations $S_2$ and $S_3$ have a low sensitivity to the pink colouring phenomenon, in contrast to $S_1$.

In the light of the various standard values exemplified above it appears that the composition $S_3$ in accordance with the invention offers the best compromise between thermalstability, colour and pink colouring (fastness to light).

We claim:

1. A composition for stabilizing chlorine-containing polymers, said composition comprising:
   (a) an unpurified crude product from a condensation reaction of an ester with a ketone in the presence of an alkaline agent, said unpurified crude product comprising between 10 and 95% by weight of beta-diketone and at least 5% by weight of by-products from the condensation reaction; and
   (b) a metal acetylacetone complex,
   wherein the constituents (a) and (b) are present in a ratio between 50/50 and 1/99.

2. The composition as defined by claim 1, wherein the constituent (a) is a solid residue from crystallization of the unpurified crude product.

3. The composition as defined by claim 2, wherein the solid residue comprises between 20 and 40% by weight of beta-diketone.

4. The composition as defined by claim 1, wherein the unpurified crude product comprises between 20 and 80% by weight of beta-diketone.

5. The composition as defined by claim 1, wherein the condensation reaction is as follows:

$R_1COCHR_2H + R_3CO\text{---}OR_4 + ACat \rightarrow R_1COCHR_2COR_3 + R_4OH$ wherein ACat is an amide of a cation or a hydride of a cation; $R_1$ and $R_3$ are identical or different, and each is a hydrocarbon radical containing 1 to 30 carbon atoms; $R_2$ is hydrogen or a hydrocarbon radical containing up to 4 carbon atoms; $R_1$ and $R_2$ are optionally linked so as to form a ring; and $R_4$ is a hydrocarbon radical.

6. The composition as defined by claim 5, wherein $R_1$ and $R_3$ are each a linear or branched aralkyl or alkenyl radical containing up to 24 carbon atoms, an aralkyl radical containing 7 to 10 carbon atoms, or an aryl or cycloaliphatic radical containing up to 14 carbon atoms; and $R_4$ is an alkyl radical containing 1 to 4 carbon atoms.

7. The composition as defined by claim 1, wherein the ester is methyl stearate, the ketone is acetophenone, and the alkaline agent is sodamide.

8. The composition as defined by claim 1, wherein the constituent (a) is in solid form.

9. The composition as defined by claim 8, wherein the constituent (a) is a powder having a particle size of less than 500 μm.

10. The composition as defined by claim 9, wherein the particle size is less than 200 μm.

11. The composition as defined by claim 9, wherein the powder is obtained by precipitation in a solvent, cryogenic grinding, or spray-drying in a cold stream, concurrently or countercurrently.

12. The composition as defined by claim 1, wherein the constituent (b) is a calcium or zinc complex.

13. The composition as defined by claim 1, wherein the ratio of constituents (a) and (b) is between 20/80 and 1/99.

14. The composition as defined by claim 1, further comprising from 0.5 to 10 parts by weight of rutile titanium oxide.

15. The composition as defined by claim 14, further comprising from 3 to 8 parts by weight of rutile titanium oxide.

16. The composition as defined by claim 15, wherein the rutile titanium oxide has a particle size of between 0.1 and 0.5 μm.

17. The composition as defined by claim 1, further comprising a stabilizing additive selected from an aluminum and/or magnesium carbonate and/or sulfate, an alkali metal aluminosilicate, and calcium and/or barium stearate.

18. The composition as defined by claim 17, wherein the additive is hydrotalcite or sodium aluminosilicate.

19. In a composition for stabilizing chlorine-containing polymers which comprises (a) a beta-diketone compound and (b) a metal acetylacetonate complex, the improvement comprising:
   using an unpurified crude product from a condensation reaction of an ester with a ketone in the presence of an alkaline agent as the beta-diketone compound,
   said unpurified crude product comprising between 10 and 95% by weight of beta-diketone and at least 5% by weight of by-products from the condensation reaction,
   said composition having a ratio of constituent (a) to constituent (b) between 50/50 and 1/99.

20. A composition for stabilizing chlorine-containing polymers, said composition comprising:
   (a) a crude product from a condensation reaction of an ester with a ketone in the presence of an alkaline agent which has not undergone recrystallization, said crude product comprising less than or equal to 95% by weight of beta-diketone; and
   (b) a metal acetylacetone complex,
   wherein the constituents (a) and (b) are present in a ratio between 50/50 and 1/99.

* * * * *